(12) United States Patent
Fattal et al.

(10) Patent No.: US 8,542,355 B2
(45) Date of Patent: *Sep. 24, 2013

(54) LIGHT AMPLIFYING DEVICES FOR SURFACE ENHANCED RAMAN SPECTROSCOPY

(75) Inventors: David A. Fattal, Mountain View, CA (US); Jingjing Li, Palo Alto, CA (US); Zhiyong Li, Redwood City, CA (US); Shih-Yuan Wang, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/383,078

(22) PCT Filed: Jul. 8, 2009

(86) PCT No.: PCT/US2009/049911
§ 371 (c)(1),
(2), (4) Date: Jan. 9, 2012

(87) PCT Pub. No.: WO2011/005253
PCT Pub. Date: Jan. 13, 2011

(65) Prior Publication Data
US 2012/0113418 A1    May 10, 2012

(51) Int. Cl.
*G01J 3/44* (2006.01)
(52) U.S. Cl.
USPC .......................................... 356/301

(58) Field of Classification Search
USPC .................... 356/301, 72–73; 977/774, 932, 977/755, 954, 840; 257/13, E33.08, 330.74
See application file for complete search history.

(56) References Cited

U.S. PATENT DOCUMENTS

| | | | |
|---|---|---|---|
| 7,224,451 B2 | 5/2007 | Masayuki | |
| 7,339,666 B2 | 3/2008 | Wang et al. | |
| 7,361,313 B2 | 4/2008 | Chan et al. | |
| 7,466,407 B2 | 12/2008 | Spillane et al. | |
| 7,483,130 B2 | 1/2009 | Baumberg et al. | |
| 2007/0058686 A1 | 3/2007 | Capasso et al. | |
| 2007/0257269 A1* | 11/2007 | Cho et al. | 257/95 |

OTHER PUBLICATIONS

Cubukcu et al., "Plasmonic Laser Antennas and Related Devices", IEEE Journal of Selected Topics in Quantum Electronics, vol. 14, No. 6, Dec. 2008.
Song et al., "Large Enhancement of Fluorescence Efficiency from CdS e/Zns Quantum Dots Induced by Resonant Coupling to Spatially Surface Plasmons", Nanoletters 2005, vol. 5, No. 8, pp. 1557-1581.

* cited by examiner

*Primary Examiner* — Tarifur Chowdhury
*Assistant Examiner* — Abdullah Nur

(57) ABSTRACT

A light amplifying device for surface enhanced Raman spectroscopy is disclosed herein. The device includes a dielectric layer having two opposed surfaces. A refractive index of the dielectric layer is higher than a refractive index of a material or environment directly adjacent thereto. At least one opening is formed in one of the two opposed surfaces of the dielectric layer, and at least one nano-antenna is established on the one of the two opposed surfaces of the dielectric layer. A gain region is positioned in the dielectric layer or adjacent to another of the two opposed surfaces of the dielectric layer.

18 Claims, 4 Drawing Sheets

LIGHT AMPLIFYING DEVICES FOR SURFACE ENHANCED RAMAN SPECTROSCOPY

STATEMENT OF GOVERNMENT INTEREST

This invention has been made with Government support under Contract No. HR0011-09-3-0002, awarded by the Defense Advanced Research Projects Agency. The government has certain rights in the invention.

BACKGROUND

The present disclosure relates generally to light amplifying devices for surface enhanced Raman spectroscopy.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or biological sensing applications. However, the intrinsic Raman scattering process is very inefficient, and rough metal surfaces, various types of nano-antennas, as well as waveguiding structures have been used to enhance the Raman scattering processes (i.e., the excitation and/or radiation process described above). This field is generally known as surface enhanced Raman spectroscopy (SERS).

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Embodiments of the device disclosed herein advantageously include a gain region, which creates a large local electric field for surface enhanced Raman spectroscopy. More specifically, a dielectric layer (having grating holes or openings formed therein) scatters light incident on the device and propagates the scattered light therein, and the gain region amplifies such light, thereby enhancing the excitation, the local field, and the resulting Raman signal.

Figure 1:
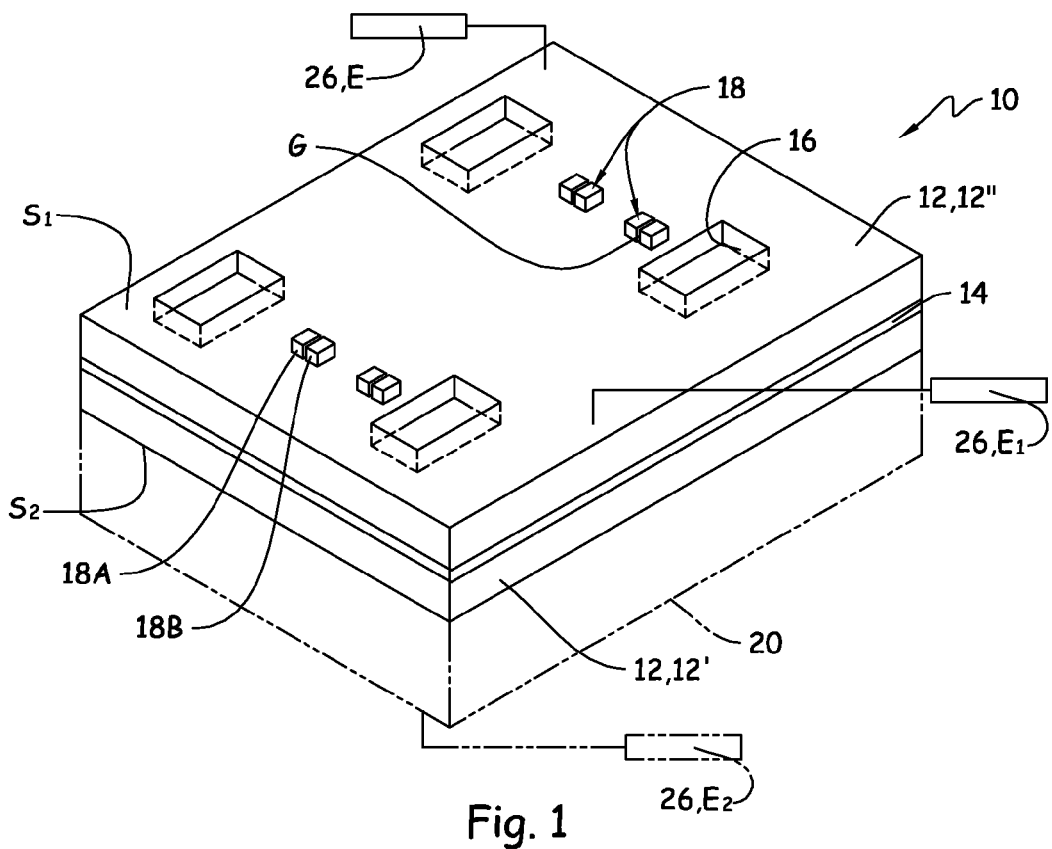
FIG. 1 is a semi-schematic perspective view of an embodiment of a light amplifying device of the present disclosure.

Referring now to FIG. 1, an embodiment of the light amplifying device 10 is depicted. The device 10 includes the previously mentioned dielectric layer 12 and gain region 14. In this embodiment, the dielectric layer 12 (or guiding layer) has two opposed surfaces $S_1$, $S_2$, one $S_1$ of which has at least one opening 16 formed therein and has at least one nano-antenna 18 established thereon, and the other $S_2$ of which is in contact with a substrate 20.

As shown in FIG. 1, both the dielectric layer 12 and the gain region 14 are established on the substrate 20. It is to be understood that the substrate 20 is selected to have a refractive index that is less than the refractive index of the dielectric layer 12. Furthermore, it is to be understood that the substrate 20 is selected so that it does not absorb at the excitation or radiating frequencies of the device 10. Non-limiting examples of suitable substrate materials include insulators (e.g., glass, quartz, ceramic, alumina, silica, silicon nitride, etc.), polymeric material(s) (e.g., polycarbonate, polyamide, acrylics, etc.), or semiconductors (e.g., silicon, InP, GaAs, InAs, $Ga_xAl_{1-x}As$ (where $0<x<1$), $In_xGa_{1-x}As_yP_{1-y}$ (where $0<x<1$, $0<y<1$)), silicon-on-insulator (SOI) substrates, nitride-on-oxide substrates (e.g., silicon nitride on oxide), or group III-V semiconductors established on silicon or SOI substrates. As shown in some of the previous examples, the substrate 20 may include multiple layers. Other examples of multi-layered substrates include GaAs on AlGaAs or GaAs on $AlO_2$.

In the embodiment shown in FIG. 1, a portion 12' of the dielectric layer 12 is grown or deposited directly on the substrate 20. Any suitable dielectric material may be used, and such dielectric materials are selected to have a higher refractive index than the refractive index of a material (e.g., the substrate 20) and/or environment (e.g., air) adjacent thereto. Non-limiting examples of suitable dielectric materials include III-V semiconductors, polymeric materials, or insulators. III-V semiconductor dielectric materials may be established via epitaxial growth; polymeric materials may be established via spin coating or other like deposition techniques; and insulators may be established via plasma enhanced chemical vapor deposition (PECVD), low pressure chemical vapor deposition (LPCVD), or other like deposition techniques.

In this embodiment, the material that makes up the gain region 14 is then grown or deposited on the portion 12' of the dielectric layer 12. The material that makes up the gain region 14 may be any material that exhibits the desirable amplifying characteristics. In an example, the gain region 14 material is selected from a III-V semiconductor material (e.g., indium gallium arsenide) or erbium doped glass.

The gain region 14 may include quantum dots (e.g., in clusters or pyramids) or quantum wells. Quantum dots of a III-V semiconductor material may be grown epitaxially, or may be synthesized separately and spun on the portion 12' in a resist-type material (non-limiting examples of which include polyimide, spin-on glass, photoresists, or the like). Quantum dots enable injected electrons and holes to recombine locally, thereby providing gain for the device 10. In an embodiment, the quantum dots have an average width ranging from about 10 nm to about 20 nm, and an average height up to about 3 nm. Quantum wells may be formed in semiconductors by having one material (e.g., gallium arsenide) sandwiched between two layers of a material with a wider bandgap (e.g., aluminum arsenide, indium arsenide, indium gallium arsenide, etc.). It is to be understood that the device 10 may include one or more quantum wells. Generally, the well material has a lower bandgap than the surrounding materials. In one embodiment, the gain region 14 includes a single well layer (where the substrate and/or dielectric layer 12 form the higher bandgap materials), and in another embodiment, the gain region 14 includes multiple well layers (where materials other than the substrate and/or dielectric layer 12 form the higher bandgap materials). Electrons and holes may be injected into the device 10, and the quantum wells act as traps for both the electrons and holes. The recombination of the electrons and holes at the quantum wells provides the gain for the device 10. The quantum wells may be grown by molecular beam epitaxy or chemical vapor deposition. It is to be understood that during establishment of the gain region 14, the gases may be changed in order to achieve the desirable layers.

As shown in FIG. 1, once the gain region 14 is established, a second portion 12" of the dielectric layer 12 is then grown or deposited thereon using the materials and techniques previously described. The total thickness of the dielectric layer 12 (including both portions 12', 12") is a fraction of the stimulating wavelength. The total thickness will depend, at least in part, on the desirable refractive index of the layer 12. Generally, a higher refractive index results in a thinner layer. In one example, the total thickness is about 200 nm, where each portion 12', 12" is about 100 nm thick.

In the embodiment shown in FIG. 1, the gain region 14 is included between portions 12', 12" of the dielectric layer 12. It is believed that this positioning maximizes the overlap of incident light waves with the gain region 14.

After the respective materials are grown or deposited to desirable thicknesses, the opening(s) 16 are formed in the portion 12" of the dielectric layer 12, and the nano-antenna(s) 18 are established on the surface $S_1$.

Figure 2:
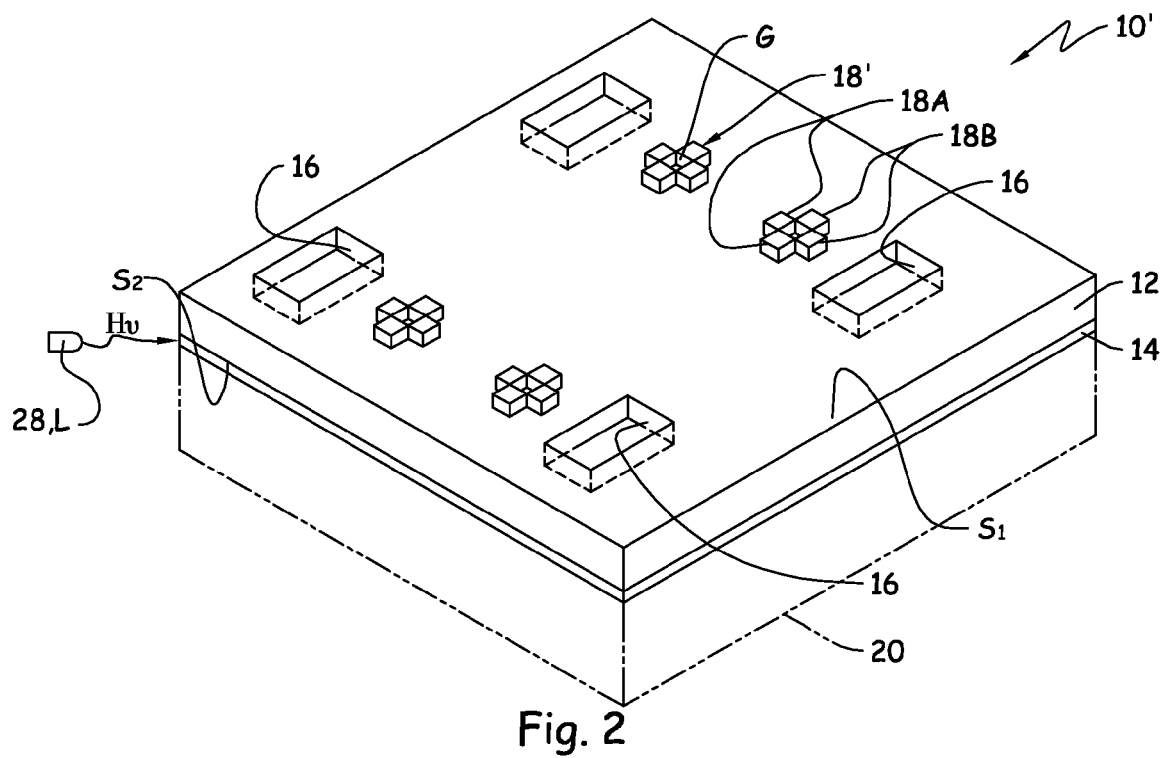
FIG. 2 is a semi-schematic perspective view of another embodiment of a light amplifying device of the present disclosure.

In an embodiment, the opening(s) 16 are formed via some form of lithography (e.g., optical lithography, electron-beam lithography, nano-imprint lithography, etc.) followed by a dry or wet etching technique commonly used in CMOS and III-V semiconductor processing. A non-limiting example of the dry etching includes Reactive Ion etching (RIE) using fluorine, chlorine, and/or methane based gas(es), and non-limiting examples of wet etching utilize HCl, HF, sodium hydroxide, ammonium hydroxide, nitric acid, and/or sulfuric acid based solutions. The opening(s) 16 generally do not extend through the entire thickness of the dielectric layer portion 12", so that light incident on the opening(s) 16 does not directly contact the gain region 14. It is desirable that the gain region 14 remain unaltered and physically separate from the etched feature(s)/opening(s) 16. This configuration advantageously avoids non-radiative recombination of the carriers. In an embodiment in which the dielectric portion 12' (or layer 12, as shown in FIG. 2) is 100 nm, the opening(s) 16 have a depth of 50 nm or less.

As shown in FIG. 1, the opening(s) 16 have a cube or a rectangular prism geometry. However, it is to be understood that the opening(s) 16 may have any suitable geometry, as long as a periodic array is formed. While a few openings 16 are shown in FIG. 1, it is to be further understood that any number of openings 16 may be formed, and that the number of openings 16 may depend, at least in part, on the number of antennas 18 to be included on the surface $S_1$. In one embodiment, the number of openings 16 ranges from an array of 10×10 to 100×100. In one non-limiting example, the array includes 10×120 openings 16. In another non-limiting example, the array includes 100×100 openings 16. Furthermore, in some instance, the array will have the same periodicity in both directions (X and Y).

As described further herein, the openings 16 scatter light (having a corresponding frequency/angle) incident thereon into the dielectric layer 12. It is to be understood that the corresponding frequency is determined, at least in part, by the periodicity of the array and the desired Raman wavelength. More particularly, the corresponding frequency may be calculated via the following equation:

$$\frac{\lambda}{\Lambda} = n_{\mathit{eff}} \pm \sin\theta$$

where $\lambda$ is the vacuum wavelength, $\theta$ is the angle of incidence, $\nabla$ is the grating period, and $n_{\mathit{eff}}$ is the effective index of the propagating mode in the guiding/dielectric layer 12.

Each nano-antenna 18 established on the surface $S_1$ of the device 10 includes at least one dimension (e.g., ½ length (i.e., the length of one segment), width, height, etc.) that is on the nano-scale (e.g., from 1 nm to 200 nm). The nano-antenna 18 may have any suitable geometry, and often includes a gap G in which the material of interest to be studied via Raman spectroscopy is introduced. The embodiment of the nano-antenna 18 shown in FIG. 1 is a linear antenna (i.e., it extends in a single direction, with no curve or bend). The linear nano-antenna 18 includes two wire segments $18_A$, $18_B$ having the gap G positioned therebetween.

Such wire segments $18_A$, $18_B$ (and thus optical antenna 18) are often made from plasmonic materials (e.g., noble metals such as gold and silver). It is to be understood that other nano-antenna 18 geometries may also be used. Non-limiting examples of such other geometries are cross antennas (shown in FIG. 2), bow-tie antennas, and elliptic, spherical, or faceted nanoparticle dimer antennas. The dimer antennas 18 include two metallic particles that touch or have a small gap (e.g., less than 10 nm) therebetween. It is to be understood that the geometry of the antennas 18 may be altered such that it resonates at a desirable frequency.

The nano-antennas 18 may be formed via a lithography technique (e.g., optical lithography, electron-beam lithography, nano-imprint lithography, photo-lithography, extreme ultraviolet lithography, x-ray lithography, etc.), or via a combination of deposition and etching techniques, or via a combination of deposition and lift-off techniques, or via direct deposition techniques (e.g., using focused ion beam (FIB) or plating). In one non-limiting example, the antennas 18 are defined via a combination of lithography, metal evaporation, and lift-off techniques.

As shown in FIG. 1, one embodiment of the device 10 also includes an electrical pump 26. The electrical pump 26 includes a pair of contacts or electrodes E, $E_1$ or E, $E_2$ that are operatively connected to the device 10 in a manner sufficient to supply electrical energy to the gain region 14. As shown in FIG. 1, both electrodes E, $E_1$ may be in electrical communication with one portion 12' of the dielectric layer 12, or one electrode E may be in electrical communication with the portion 12' while the other electrode $E_2$ is in electrical communication with the substrate 20. One or both of the electrodes E, $E_1$, $E_2$ may be metal (e.g., gold, platinum, aluminum, silver, tungsten, copper, etc.). Although individual electrodes E, $E_1$ or E, $E_2$ are shown with rectangular cross-sections, it is to be understood that electrodes E, $E_1$ or E, $E_2$ may also have circular, elliptical, or more complex cross-sections. The electrodes E, $E_1$ or E, $E_2$ may also have many different widths or diameters and aspect ratios or eccentricities. Furthermore, the electrodes E, $E_1$ or E, $E_2$ may be acquired in a usable state or may be fabricated using conventional techniques, such as photolithography or electron beam lithography, or by more advanced techniques, such as, e.g., imprint lithography. In one embodiment, the thickness of each electrode E, $E_1$, $E_2$ ranges from about 5 nm to about 30 nm.

Metal electrodes E, $E_2$ may also be connected to highly doped semiconductors to form an ohmic contact (i.e., a contact with very low resistance). When a III-V semiconductor is used in conjunction with the metal electrode E, $E_2$ to form ohmic contacts, it is to be understood that any suitable dopant may be used during epitaxial growth to form the back contact (e.g., which is adjacent to both the substrate 20 and electrode $E_2$), or during ion implantation to form the top contact (e.g., which is adjacent to both the dielectric layer 12, 12' and electrode E). It is to be understood that in this embodiment the interstitial semiconductors (e.g., those making up the dielectric layer 12 and/or the gain region 14) may also be doped.

In still another embodiment, electrical pumping into a III-V gain region 14 may be accomplished using a vertical p-n junction. For example, a highly p-doped region may be established on the surface $S_1$ and connected to metal vias, and the substrate 20 may be highly n-doped and connected to another metal contact. In this embodiment, the interstitial semiconductors (e.g., those making up the dielectric layer 12 and/or the gain region 14) may be slightly doped to decrease series resistance.

While the electrical pump 26 is shown in FIG. 1, it is to be understood that an optical pump 28 (shown and further described in reference to FIG. 2) may be used to supply energy to the gain region 14.

When the device 10 is properly designed (including desirable opening 16 and nano-antenna 18 geometries), light having a corresponding frequency/angle is amplified. During its use, the electric field in a certain small area (i.e., the hot spot) around the antenna 18 is much stronger than that of the incident electromagnetic (EM) wave in a certain frequency range at or around the resonant frequency of the antenna 18. As such, when a material of interest (or an object made of the material of interest) is placed at the hot spot, the Raman scattering of this material is greatly enhanced in the excitation process, the radiation process, or, in some instances, both the excitation and radiation processes. This is due, at least in part, to the presence of the dielectric layer 12 (including the opening(s) 16 and the gain region 14. During use of the device 10, the material of interest is placed in the gap of the nano-antenna 18 or at any hot spot of the nano-antenna 18; light of a stimulating/exciting wavelength is directed toward the surface $S_1$; and electrical energy is applied to the gain region 14 (which provides gain to the device 10). The light incident on the opening(s) 16 is scattered in the dielectric layer 12, and becomes trapped in the dielectric layer 12. The scattered, trapped light waves propagate along the dielectric layer 12 and bounce between the various openings 16. The trapped propagated waves are amplified by the electrically activated gain region 14. These amplified waves enhance the excitation of the material in the hot spot, and generate a large local electric field for Raman spectroscopy. It is to be understood that the electrical power pumped into the device 10 is in addition to the power already present in the exciting beam. The SERS signal in the presence of the pumped gain will increase monotonically with extra power spent.

Referring now to FIG. 2, another embodiment of the device 10' is depicted. Like the embodiment shown in FIG. 1, both the dielectric layer 12 and the gain region 14 in this embodiment are established on the substrate 20. Unlike the embodiment shown in FIG. 1, however, the gain region 14 in this embodiment is positioned adjacent to the surface $S_2$, $S_1$ that is opposite to the surface $S_1$, $S_2$ toward which the excitation/stimulation light is directed. As such, the gain region 14 is established between the substrate 20 and the dielectric layer 12, and is not sandwiched between portions 12', 12" of the dielectric layer 12.

Any suitable dielectric material may be used, and such dielectric materials are selected to have a higher refractive index than the refractive index of a material (e.g., the substrate 20) and/or environment (e.g., air) adjacent thereto. It is to be understood that the dielectric layer 12 may be any of the materials described herein in reference to FIG. 1.

In this embodiment, both the gain region 14 and the substrate 20 are selected to have a refractive index that is less than the refractive index of the dielectric layer 12. The substrate 20 is also selected so that it does not absorb at the excitation or radiating frequencies of the device 10'. Examples of suitable substrate materials and gain region materials are described in reference to FIG. 1.

In this embodiment, the material that makes up the gain region 14 is grown or deposited on the substrate 20. The material that makes up the gain region 14 may be any of those described herein. Similar to the embodiment described in FIG. 1, the gain region 14 may include quantum dots (e.g., in clusters or pyramids) or quantum wells. Any of the methods and/or materials disclosed herein for the quantum dot or quantum wells may be utilized in this embodiment as well.

As shown in FIG. 2, once the gain region 14 is established, the dielectric layer 12 is then grown or deposited thereon using the materials and techniques previously described. The total thickness of the dielectric layer 12 is a fraction of the stimulating wavelength. As previously mentioned, the total thickness will depend, at least in part, on the desirable refractive index of the layer 12, and the higher the refractive index, the thinner the layer 12 will be. In one example, the total thickness is about 200 nm. In another example, the total thickness is 100 nm. The embodiment of the device 10' shown in FIG. 2 may be less efficient than the embodiment of the devices 10, 10" shown respectively in FIGS. 1 and 3, at least in part because of the positioning of the gain region 14; however, such device 10' may be easier to manufacture than the devices 10 and 10".

After the respective materials are grown or deposited to desirable thicknesses, the opening(s) 16 are formed in a portion of the dielectric layer 12 using the methods described herein, and the nano-antenna(s) 18' are established on the surface $S_1$ using the materials and methods described herein. In the embodiment shown in FIG. 2, the nano-antenna 18' includes two respective antennas (each of which includes two segments $18_A$ and $18_B$) that cross at a non-zero angle and share a gap G at their intersection.

As shown in FIG. 2, one embodiment of the device 10' also includes an optical pump 28. The optical pump 28 includes at least one light source L that is operatively positioned relative to the device 10' in a manner sufficient to supply optical energy to the gain region 14. As shown in FIG. 2, the light source L is in optical communication with one area of the gain region 14. It is to be understood that multiple light sources L may be used to supply energy to the gain region 14, and that such additional light sources (not shown) may be positioned such that light is directed toward other areas of the gain region 14. Non-limiting examples of the light source L include a light-emitting diode (LED) or a laser, the frequency of which depends upon the gain region 14 used. As one example, erbium doped glass is pumped at 980 nm or 1,480 nm, and exhibits gain in the 1,550 nm region.

When the device 10' is properly designed (including desirable opening 16 and nano-antenna 18' geometries), light having a corresponding frequency/angle is amplified. During its use, the electric field in a certain small area (i.e., the hot spot) around the antenna 18' is much stronger than that of the incident electromagnetic (EM) wave in a certain frequency range at or around the resonant frequency of the antenna 18'. As such, when a material of interest (or an object made of the material of interest) is placed at the hot spot, the Raman scattering of this material is greatly enhanced in either the excitation process, the radiation process or, in some instances, both the excitation and radiation processes. This is due, at least in part, to the presence of the dielectric layer 12 (including the opening(s) 16) and the gain region 14. More specifically, during use of the device 10', the material of interest is placed in the gap G of the crossed nano-antenna 18' (or at any hot spot of the nano-antenna 18'), light of a stimulating/exciting wavelength is directed toward the surface $S_1$, and optical energy is applied to the gain region 14 (which provides gain to the device 10'). Light (from an excitation/stimulation light source, not shown) incident on the opening(s) 16 is scattered in the dielectric layer 12, and becomes trapped in the dielectric layer 12. The scattered, trapped light waves propagate along the dielectric layer 12 and bounce between the various openings 16. The trapped propagated waves are amplified by the optically activated gain region 14. These amplified waves enhance the excitation of the material in the hot spot, and generate a large local electric field for Raman spectroscopy. It is to be understood that the optical power pumped into the device 10 is in addition to the power already present in the exciting beam. The SERS signal in the presence of the pumped gain will increase monotonically with extra power spent.

Figure 3:
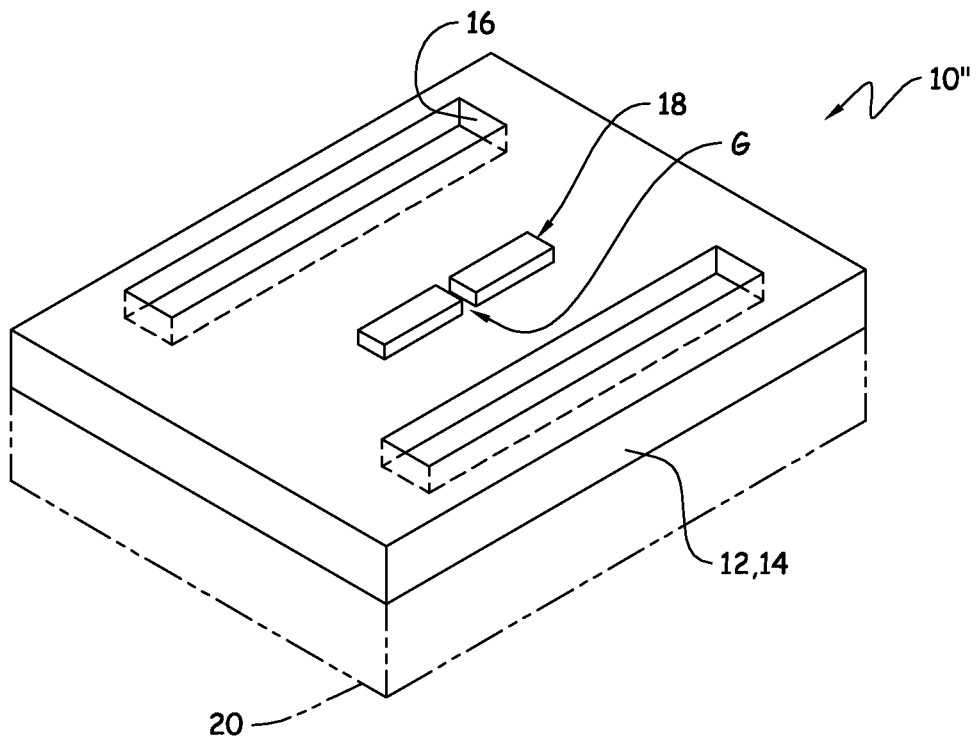
FIG. 3 is a semi-schematic perspective view of still another embodiment of a light amplifying device of the present disclosure.

Referring now to FIG. 3, still another embodiment of the device 10" is depicted. Similar elements and components to those described in reference to FIGS. 1 and 2 are included in the device 10" of FIG. 3, and thus the materials and techniques described in connection with such devices 10, 10' are suitable for the device 10" shown in FIG. 3. While the electrical and/or optical pump 26, 28 is not shown in FIG. 3, it is to be understood that either of such pumps 26, 28 may be used to supply energy to the gain region 14.

In the embodiment of the device 10" shown in FIG. 3, the gain region 14 is formed in all or a portion of the dielectric layer 12. The material selected for the gain region 14 may be implanted into the dielectric layer by ion implantation. One non-limiting example of this embodiment is erbium ions introduced into a glass layer. It is to be understood that the voltage used during ion implantation may be controlled in order to control the depth at which the ions are implanted into the dielectric layer 14. In some instances, the ions may be implanted into the entire depth of the dielectric layer 12, and thus the gain region 14 is present throughout the dielectric layer 12. In other instances, the ions may be implanted into a portion of the depth of the dielectric layer 12, and thus the gain region 14 is present in that portion of the dielectric layer 12.

Figure 5A:
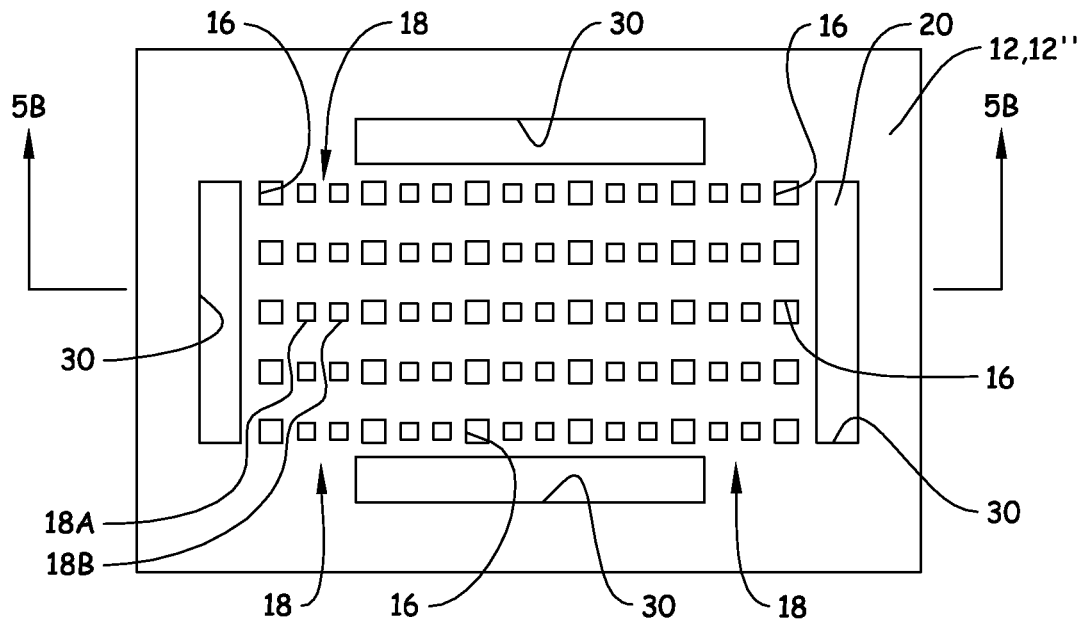
FIGS. 5A and 5C are top views of an embodiment of the light amplifying device before and after a wet etching process used to form a suspended device.
Figure 5B:
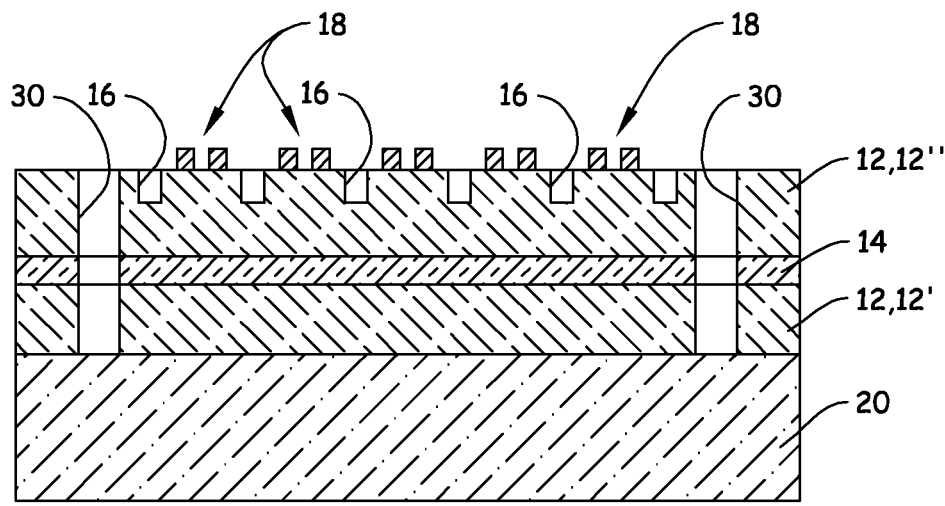
FIG. 5B is a cross-sectional view, taken along line 5B-5B of FIG. 5A, of the embodiment of the light amplifying device before wet etching.

It is to be understood that the components 12, 14, 16, and 18 or 18' may not be established on the entire substrate 20, but rather may be suspended over a substrate 20. An example of this is shown in FIG. 5D. Together, FIGS. 5A and 5C or FIGS. 5B and 5D illustrate the formation of such a device 10'''. The embodiment shown in FIGS. 5A and 5B is similar to the device 10 shown in FIG. 1, except that an array of 6×6 openings 16 is included. It is to be understood that the array of openings 16 may, in some instances, have the same X and Y periodicity.

Furthermore, in this embodiment, openings 30 are formed through the entire depth of the dielectric layer 12 to expose the substrate 20. Such openings 30 may surround the components 12, 14, 16, 18. These openings 30 may be formed in a similar manner to that used for openings 16, for example, via some form of lithography followed by dry or wet etching.

After the openings 30 are formed, an etchant that selectively etches the substrate 20, and not the dielectric layer 12 or the gain region 14, is exposed to the substrate 20 through the openings 30. This etchant removes a portion of the substrate 20. Etching the substrate 20 in such a manner results in the openings 16, the nano-antennas 18, and layers 12 and 14 (upon which such components 16, 18 are formed or established) being suspended over a void 32 formed in the substrate 20. The time for which the substrate 20 is exposed to the etchant will dictate how much of the substrate 20 is removed. Generally, the etching time depends upon the concentration and the type of etchant used. In one embodiment the etching time is less than or equal to 5 minutes. In a non-limiting example, when the dielectric layer 12 is GaAs and the substrate 20 is AlGaAs, hydrofluoric acid (HF) may be a suitable etchant. While the void 32 shown in FIG. 5D has a well defined geometry, it is to be understood that the void 32 may have any regular or non-regular geometry. As one non-limiting example, the sidewalls of the void 32 may be slanted instead of rounded.

Figure 5C:
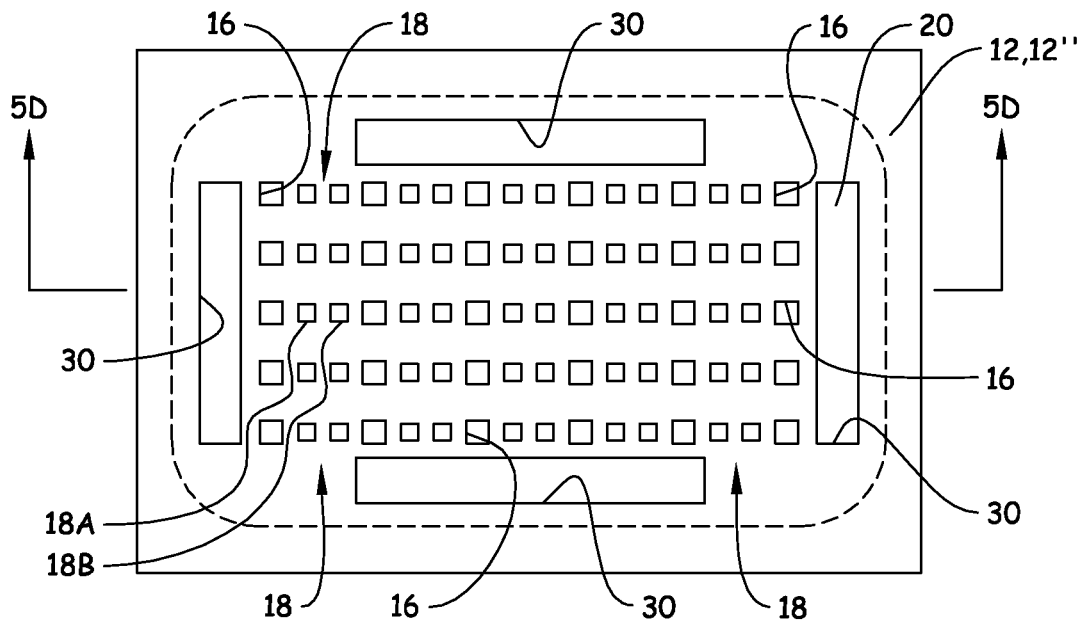
Figure 5D:
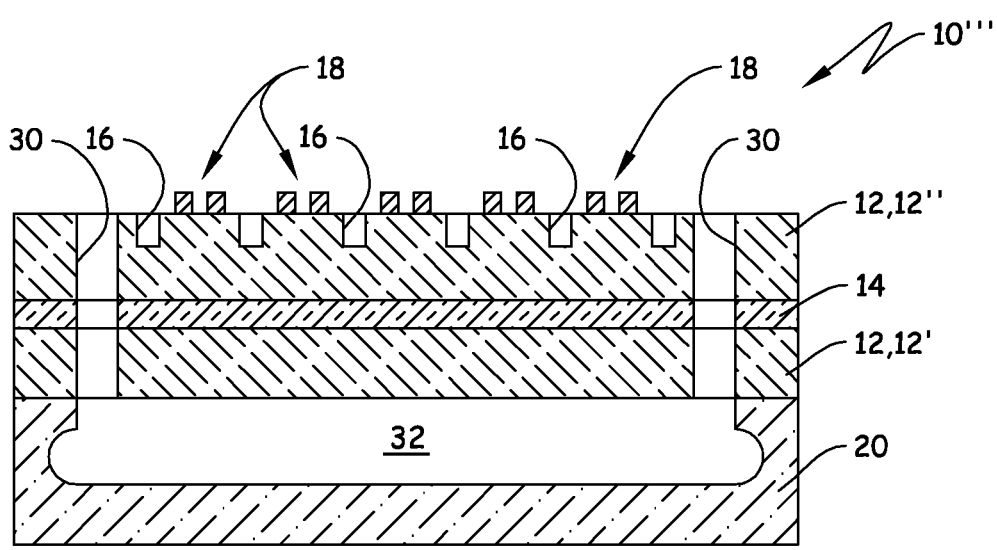
FIG. 5D is a cross-sectional view, taken along line 5D-5D of FIG. 5C, of the embodiment of the light amplifying device after wet etching (i.e., a suspended light amplifying device).

The resulting suspended device 10''' is shown in FIGS. 5C (top view) and 5D (cross-sectional view). In this embodiment, it is to be understood that the refractive index of the dielectric layer 12 is higher than the refractive index of the surrounding environment (e.g., air in the void 32).

Figure 4:
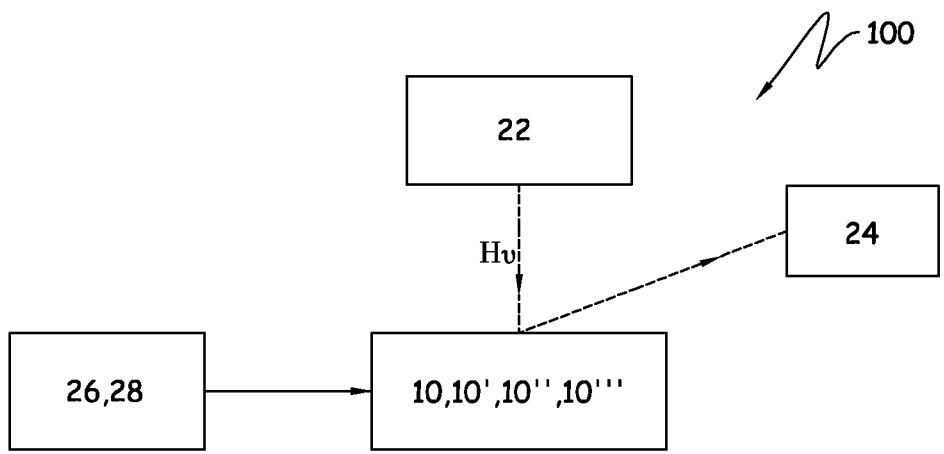
FIG. 4 is a schematic diagram of an embodiment of a system including the light amplifying device(s) disclosed herein.

The devices 10, 10', 10", 10''' disclosed herein are suitable for use in standard Raman detection procedures. The system 100 for such a procedure is shown schematically in FIG. 4 and includes the device 10, 10', 10", 10''', the electrical or optical pump 26, 28, a stimulation/excitation light source 22, and a detector 24. In some embodiments, analyte molecules or particles are distributed in the gap or at the hot spot of the nano-antenna(s) 18, 18' and are subsequently subjected to laser excitation of suitable stimulating/exciting wavelengths from the light source 22. As previously mentioned, the light incident on the opening(s) 16 is scattered in the dielectric layer 12 and becomes trapped within the dielectric layer 12. The trapped light is amplified by the gain layer 14. This amplified light enhances the excitation of the molecule(s)/particle(s) in or on the nano-antenna 18, 18' and the resulting Raman signals are detected using known detector(s) 24.

While several embodiments have been described in detail, it will be apparent to those skilled in the art that the disclosed embodiments may be modified. Therefore, the foregoing description is to be considered exemplary rather than limiting.

What is claimed is:

1. A light amplifying device for surface enhanced Raman spectroscopy, comprising:
    a dielectric layer having two opposed surfaces, wherein a refractive index of the dielectric layer is higher than a refractive index of a material or environment directly adjacent thereto;

at least one opening formed in one of the two opposed surfaces of the dielectric layer;

at least one nano-antenna established on the one of the two opposed surfaces of the dielectric layer; and a gain region positioned in the dielectric layer or adjacent to an other of the two opposed surfaces of the dielectric layer.

2. The light amplifying device as defined in claim 1, further comprising a substrate having the dielectric layer established directly or indirectly thereon, wherein the substrate has a refractive index that is less than the refractive index of the dielectric layer.

3. The light amplifying device as defined in claim 2 wherein the gain region is positioned in the dielectric layer, and wherein the dielectric layer is established directly on the substrate.

4. The light amplifying device as defined in claim 2 wherein the gain region is positioned adjacent to the other of the two opposed surfaces of the dielectric layer, and wherein the gain region is established directly on the substrate.

5. The light amplifying device as defined in claim 1 wherein the gain region includes at least one of quantum dots or quantum wells.

6. The light amplifying device as defined in claim 1 wherein the gain region includes a III-IV semiconductor material or erbium doped glass.

7. The light amplifying device as defined in claim 1, further comprising at least one of i) a pair of electrodes or ii) a light source configured to supply energy to the gain region.

8. A system for performing surface enhanced Raman spectroscopy, comprising:

a light amplifying device, including:

a dielectric layer having two opposed surfaces, wherein a refractive index of the dielectric layer is higher than a refractive index of a material or environment adjacent thereto;

at least one opening formed in one of the two opposed surfaces of the dielectric layer;

at least one nano-antenna established on the one of the two opposed surfaces of the dielectric layer; and a gain region positioned in the dielectric layer or adjacent to an other of the two opposed surfaces of the dielectric layer;

an energy source operatively configured to supply energy to the gain region; and a light source operatively configured to direct light toward the at least one nano-antenna of the light amplifying device.

9. The system as defined in claim 8, further comprising a detector operatively positioned to detect an enhanced Raman signal from a material of interest positioned adjacent to at least a portion of the at least one nano-antenna of the light amplifying device.

10. The system as defined in claim 8 wherein the light amplifying device further includes a substrate having the dielectric layer established directly or indirectly thereon, wherein the substrate has a refractive index that is less than the refractive index of the dielectric layer.

11. The system as defined in claim 10 wherein the gain region is positioned in the dielectric layer, and wherein the dielectric layer is established directly on the substrate.

12. The system as defined in claim 10 wherein the gain region is positioned adjacent to the other of the two opposed surfaces of the dielectric layer, and wherein the gain region is established directly on the substrate.

13. A method for making a light amplifying device for surface enhanced Raman spectroscopy, the method comprising:

forming at least one opening in one of two opposed surfaces of a dielectric layer having a refractive index that is higher than a refractive index of a material or environment configured to be directly adjacent thereto;

establishing at least one nano-antenna on the one of the two opposed surfaces of the dielectric layer; and establishing a gain region in the dielectric layer or adjacent to an other of the two opposed surfaces of the dielectric layer.

14. The method as defined in claim 13, further comprising operatively positioning an energy source such that it is selectively configured to supply energy to the gain region, the energy source being selected from i) a pair of electrodes; and ii) a light source.

15. The method as defined in claim 13, further comprising establishing the dielectric layer directly or indirectly on a substrate having a refractive index that is less than the refractive index of the dielectric layer.

16. The method as defined in claim 15 wherein the establishing of the gain region in the dielectric layer and the establishing of the dielectric layer directly on the substrate are accomplished by:

growing a first portion of the dielectric layer directly on the substrate;

growing quantum wells to form the gain region on the first portion of the dielectric layer; and growing a second portion of the dielectric layer on the gain region, wherein a surface of the second portion of the dielectric layer is the one of the two opposed surfaces of the dielectric layer.

17. The method as defined in claim 15 wherein the establishing of the gain region adjacent to the other of the two opposed surfaces is accomplished by:

depositing a material that forms the gain region directly on the substrate; and then depositing the dielectric layer on the gain region.

18. The method as defined in claim 15 wherein the establishing of the gain region in the dielectric layer is accomplished via ion implantation.

* * * * *